United States Patent
Liu et al.

(12) 
(10) Patent No.: US 6,645,718 B2
(45) Date of Patent: Nov. 11, 2003

(54) DNA SAMPLE COLLECTION FOR IDENTIFICATION

(75) Inventors: Ming-Sun Liu, Brea, CA (US); Varouj Amirkhanian, La Crescenta, CA (US); Sing-Tien Chiang, Oceanside, CA (US)

(73) Assignee: Biocal Technology, Inc., Orange, CA (US)

( * ) Notice: Subject to any disclaimer, the term of this patent is extended or adjusted under 35 U.S.C. 154(b) by 0 days.

(21) Appl. No.: 09/726,957

(22) Filed: Nov. 30, 2000

(65) Prior Publication Data

US 2002/0064776 A1 May 30, 2002

(51) Int. Cl.$^7$ ............................ C12Q 1/68; A01N 1/02; C07H 21/04; G06F 17/60
(52) U.S. Cl. ............................ 435/6; 435/2; 435/91.1; 435/91.2; 536/23.1; 536/23.5; 705/3; 705/4; 705/43; 705/80; 235/379
(58) Field of Search ............................ 435/216, 91.1, 435/91.2; 705/3, 4, 431, 80; 235/379

(56) References Cited

U.S. PATENT DOCUMENTS

| | | | |
|---|---|---|---|
| 4,208,795 A | | 6/1980 | Muhlemann et al. ....... 433/203 |
| 6,199,754 B1 | * | 3/2001 | Epstein ..................... 235/379 |
| 6,213,391 B1 | * | 4/2001 | Lewis ........................ 235/380 |
| 6,291,171 B1 | * | 9/2001 | Ricciardi et al. ........... 206/223 |

OTHER PUBLICATIONS

Evans, J. (American Banker (1992) pp. 3–4).*
Trembly (National Underwriter Property & Casualty/Risk & Benefits Management Edition, Jun. 14, 1999).*
Independent Insurance Agent, The Do's & Don'ts of Travel Insurance, Date unknown, 6 pages.
Canfield & Hansrote, Reducing Post Aviation Accident Trauma, Spring 1999, 2 pages.
DNA Indentification Systems, DNA Home Collection and Storage Kit, Date unknown, 3 pages.
Kessler, TWA Probe: Submarines Off Long Island, Date unknown, 2 pages.
Lander, Use of DNA in Identification, Date unknown, 7 pages.
Betsch, DNA Fingerprinting in Human Health and Society, Date unknown, 4 pages.
Lopez, Identifying the Victims: Disaster–Mortuary Team Helps Speed the Process, Jan. 14, 1997, 2 pages.
Nolo.com, Benefits and Limitations of Travel Insurance, Date unknown, 6 pages.
Davey & Manier, Painstaking Task Ahead as Victims' IDs Sought, Mar. 18, 1999, 3 pages.
CNN, Victims' Families Seek Faster, Better Information, Nov. 20, 1996, 3 pages.

* cited by examiner

*Primary Examiner*—Kenneth R. Horlick
*Assistant Examiner*—Alexander H. Spiegler
(74) *Attorney, Agent, or Firm*—Liu & Liu

(57) ABSTRACT

A process of collecting a sample of DNA from an individual for short-term or long term storage in the event that the DNA is required to identify the individual in the event of a cataclysmic accident. The collection of DNA sample from the individual begins with the completion of an application, for example for flight insurance, which is conveniently located at the airport, through a travel agent, etc. Upon completion of the application, a method of payment is determined and the DNA sample is collected. Preferably, the individual collects his or her DNA sample using a non-invasive approach such as swabbing the inside of his/her cheek and gum line. The DNA sample is then placed in a container and held in storage for a duration appropriate for the anticipated span of the activity or for a predetermined fixed term. At the conclusion of the activity, the DNA sample is either disposed of or returned to the individual for future use. If the individual is involved in an accident resulting in a cataclysmic death, the DNA is retrieved to aid in the identification of the deceased.

14 Claims, 3 Drawing Sheets

DNA SAMPLE COLLECTION FOR IDENTIFICATION

BACKGROUND OF THE INVENTION

1. Field of the Invention

This invention relates in general to collecting DNA samples for personal identification, and more particularly to collecting DNA samples for the identification of an individual involved in cataclysmic accident.

2. Description of the Related Art

Positive identification of an individual is important for example, after an accident for insurance claims. Flight insurance and travel insurance may provide a form of security for travelers that are afraid that their loved ones may suffer financial hardships if something were to happen to them. For example, flight insurance is a type of travel accident insurance that provides life insurance benefits only in the event of a fatality involving an aircraft. Travel accident insurance provides life insurance benefits for accidents that occur while traveling on covered public or common carrier transportations, including plane, bus, taxicab, subway, ferry, cruise ship, etc. Typically, frequent travelers are likely to purchase some type of travel accident insurance. In the event that the traveler is killed in an accident, positive identification of the traveler is important because insurance companies are often hesitant to confirm a person's death. Further, positive identification is important for the family members of the deceased victim, since it provides a sense of certainty and relief for the grieving family members to know the identity of the deceased whom they are laying to rest.

The traditional method of identifying an accident victim typically involves one or more of the following: visual identification, identification by item of clothing, written identification, identification by jewelry, identification by finger print, identification by medical and dental records, and identification by exclusion. Identification by examining the victim's teeth is commonly done, however if the teeth are destroyed or not found, forensic falls back to the victim's bones because the human skeleton and features may uniquely identify an individual. This identification process is inherently inaccurate, slow and tedious, resulting in long delays in identifying the victim or even the inability to identify him or her.

DNA fingerprinting is one of the best approaches to positive identification because it is accurate and fast, when compared to traditional methods as described above. DNA is an abbreviation for deoxyribonucleic acid and is made up of four chemicals, called bases that are abbreviated A, T, C, and G. DNA is composed of millions of these bases and their combination or DNA fingerprint is unique to each person. DNA fingerprinting for personal identification is useful for forensic applications such as identifying murder victims and non-forensic applications such as diagnosing inherited disorders and identifying an individual involved in cataclysmic accidents.

However, DNA is not typically collected from a person in anticipation of death requiring identification of the remains. For an individual engaged in an activity such as traveling, the problem of DNA collection is a challenge. The process of collecting DNA should be painless, quick, and foolproof for the individual. At the same time, the company responsible for the DNA collection would be concerned about the handling cost, ease of use, and the integrity of the DNA sample, upon collection from the individual. What is needed is DNA sample collecting process that is practical for both the individuals providing the DNA sample and the company providing the service.

SUMMARY OF THE INVENTION

The present invention is directed to a method of collecting a sample of DNA from an individual for short-term or long-term storage in the event that the DNA is required to identify the individual in the event of a cataclysmic accident. DNA sample(s) are collected from the individuals or group of people, by a non-invasive means, prior to engaging in an activity that may compromise the individual. In a specific embodiment, the DNA sample is collected with the specific purpose for the activity. For example, the DNA sample is collected at a time between the individual deciding to undertake the activity and actually undertaking the activity. More specifically, the DNA sample may be collected substantially just before the start of the activity.

The DNA sample is placed in a container or bag and held in short-term or long-term storage for the anticipated span of the activity. At the conclusion of the activity, the DNA sample is disposed of unless the individual is in an accident resulting in a cataclysmic death and identification by means of DNA is needed. If there are no accidents and the traveler decides to use his/her DNA for other purpose, it is treated accordingly.

DETAILED DESCRIPTION OF THE PREFERRED EMBODIMENT

The present description is of the best presently contemplated mode of carrying out the invention. This description is made for the purpose of illustrating the general principles of the invention and should not be taken in a limiting sense. The scope of the invention is best determined by reference to the appended claims.

The present invention is directed to a method of collecting a DNA sample of an individual for short-term or long-term storage. In the event of a cataclysmic accident, the individual can be identified by his or her stored DNA. To facilitate an understanding of the principles and features of the present invention, they are explained herein below with reference to its deployments and implementations in illustrative embodiments. By way of example and not limitation, the present invention is described herein-below in reference to examples of deployments and implementations for collecting DNA samples for personal identification in connection with travel-related activities.

The present invention can find utility in a variety of implementations without departing from the scope and spirit of the invention, as will be apparent from an understanding of the principles that underlie the invention. It is understood that the concept of the DNA sample collecting process of the present invention may be applied to various travel related activities from cruise ships, to transportation means such as subways, trains, taxis, etc, and non-travel related activities such as extreme sports and high risk occupational activities (e.g. mining, law enforcement, fire fighting, combat for soldiers).

Figure 1:
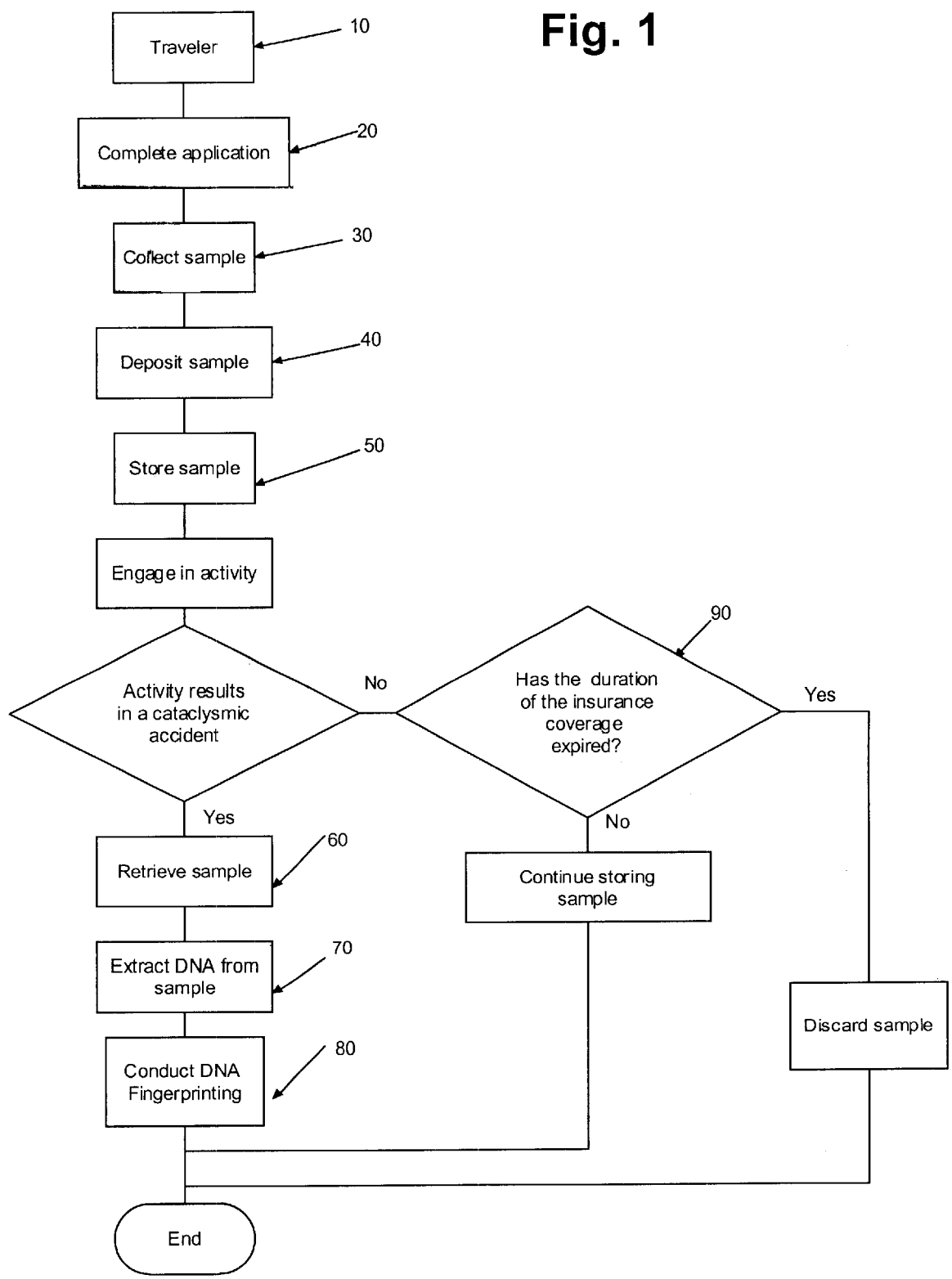
FIG. 1 is a block diagram of the process of acquiring travel insurance and personal identification using DNA in connection with travel related accidents, in accordance with one embodiment of the present invention.

With reference to FIG. 1, there is described the general process by which a DNA sample of a traveler is collected, stored, and used to identify the traveler in the event of a cataclysmic accident. In the following embodiment, the traveler is interested in purchasing short-term life insurance prior to his/her plane flight. The traveler completes the necessary short-term life insurance application, collects and deposits the necessary DNA sample, then proceeds with the travel activity. At the end of the activity, the DNA sample is discarded unless the traveler is killed in an accident and the DNA sample is needed to aid in identifying the traveler. The individual steps are further detailed in the following descriptions.

Application

In this example, the traveler purchases a short-term insurance policy substantially just prior to his or her flight. The application may be taken at a designated location at the airport terminal. For those who purchase insurance ahead of scheduled travel, the application process may be completed at the time and location of such purchase, e.g., at a travel agent's office at the time tickets and insurance are being purchased, or a travel insurance agent's office at the time a long-term travel insurance is being purchased. The DNA collection process described below is also applicable for other than purchase of insurance coverage, such as for passenger identification administers by airlines, either for a fee or free of charge to the passengers.

The collection of DNA sample from a traveler begins with the traveler completing an application form for the desired insurance service (Block 20). The application can be completed in a number of ways including, verbally by telephone, filling out a hard copy of the form, or by entering information via keyboard and terminal. The application typically includes questions regarding personal information, different plans available and fees, payment method, activity information, anticipated length of travel, terms, conditions, etc. Payment method can be made by using cash, a credit card, check, debit card, etc. The traveler would also have to agree to any legal issues regarding the testing of DNA. Upon completion of the application, the customer or someone prepares a sample of the traveler's DNA.

Collection of DNA Sample

Figure 2:
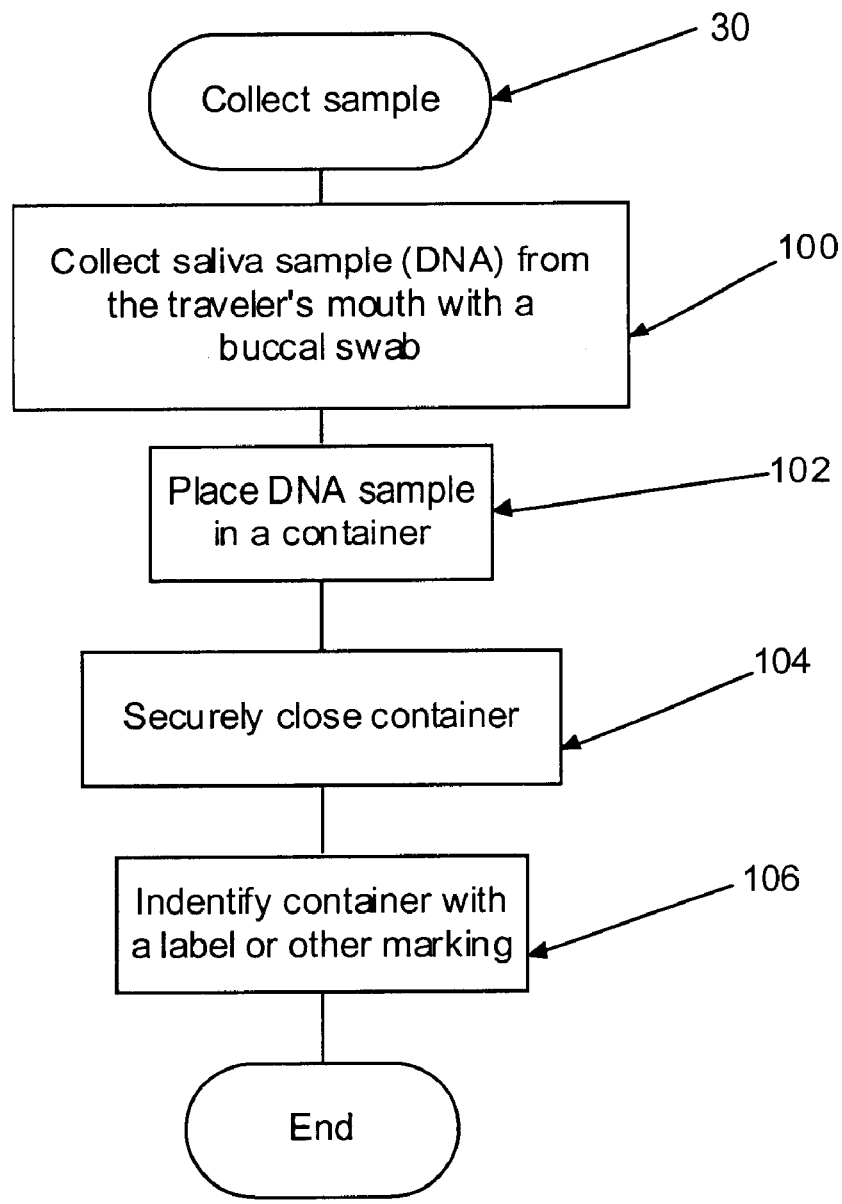
FIG. 2 is a detailed block diagram of the DNA sample collection process in accordance with one embodiment of the present invention.
Figure 3:
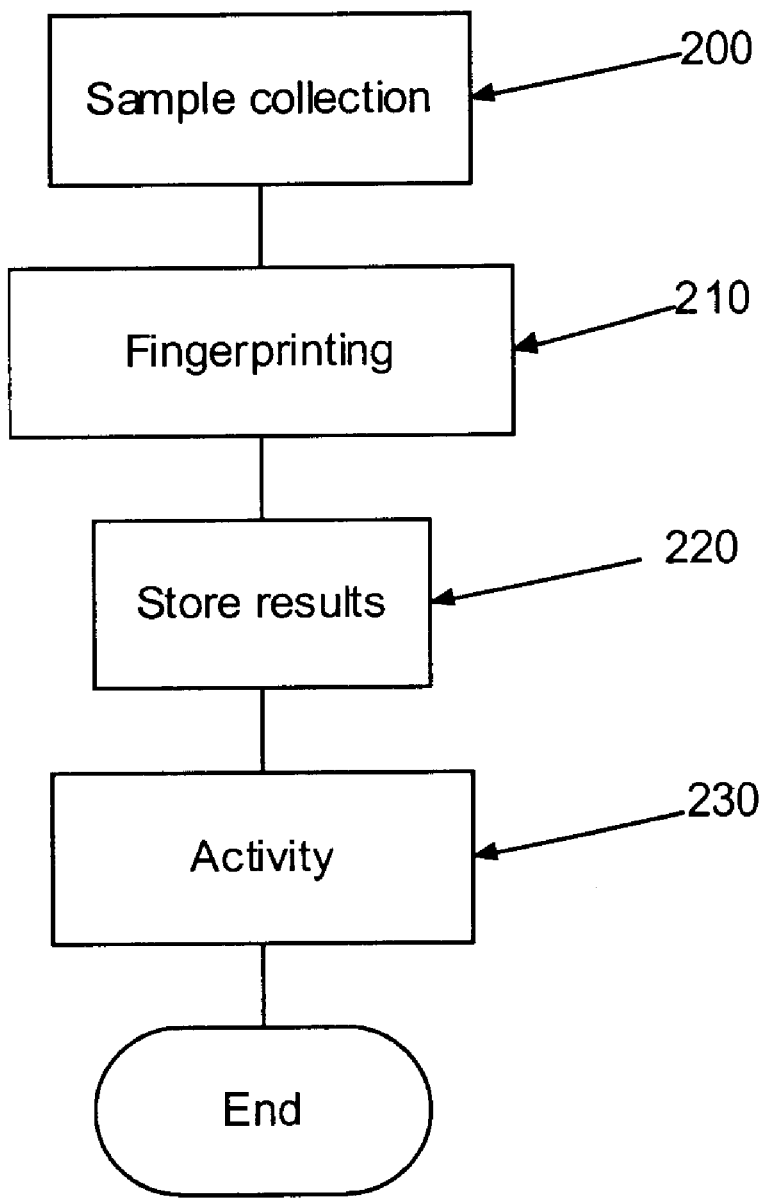
FIG. 3 is a block diagram of the process of acquiring personal identification using DNA for other uses, in accordance with a second embodiment of the present invention.

Once the application is completed, one or several samples of DNA are collected from the traveler (Block 30). The sample collection process is illustrated schematically in FIG. 2. The DNA collection is preferably accomplished by using a gentle non-invasive approach such as, having the traveler collect samples of salvia, hair, tear, cerumen, skin, or chemical etch. Salvia collection for example, is performed by having the traveler swab the inside of his/her cheek and gum line by using a buccal swab, stick, or other tool (Step 100). This is the preferred method because it is not an invasive method, such as taking blood samples. Also, the handling of saliva is less bio-hazardous compared to other bodily fluids. The saliva sample contains DNA samples. The DNA sample is then placed in a secure container/envelope and sealed (Step 102,104). The container should be moisture proof, and preferable hermetically sealed. Container could be constructed from any suitable material. The container/envelope must be clearly identified and labeled, typically with written text, bar coding, or other identification means (Step 106).

Deposit of DNA Sample

Once the DNA sample has been collected and labeled, it is associated with the application form such as, by placing it in another protected envelope/box along with the completed application form. Once the envelope/box is sealed, it is either placed in a drop-box, given to a collection agent (e.g., acting on behalf of the insurance company), or delivered to the designated site using a carrier (Block 40). Steps must be taken to assure that the envelope/box is not tampered with or damaged. Depending on the deposit method used, other transactional tasks such as payment may be required at the time of deposit. A machine similar to an automatic banking machine (ATM, automatic teller machines) may be used to deposit the sample, as well as attend to the transactional issues such as payment. Such automated machine may provide a deposit slot to accept the sample packet, stamp identification information, reference number etc. on the packet, generate a receipt, etc.

Collection and Storage of DNA Sample

The DNA packet is collected (e.g., by the insurance company or its agent) from the drop-off location (e.g., drop-box or automated machine described above) and stored at a storage facility in a controlled environment to prevent the DNA sample from degrading (Block 50). The storage facility will typically be responsible for the indexing and storage of the samples. In the case of using a drop-box, a routine pickup should be implemented to prevent the drop-box from exceeding the holding capacity.

DNA Sample Retrieval or Disposal

At the conclusion of the travel activity (or the insured activity), if the DNA sample is not required for current identification, it should be disposed of in accordance with the option selected or designated by the traveler during the application process (e.g., checking a box in the application form). Alternatively, the sample may be disposed of after a default period specified by the insurance company and stated on the form if the traveler did not select an option for disposing the sample (Block 90). In the event the traveler is involved in a cataclysmic accident in which the DNA is needed to identify the traveler, the saliva sample is retrieved from storage (e.g., by the insurance company or its agent) (Block 60) and the DNA is extracted (Block 70) and processed by known DNA identification processes (Block 80).

DNA sample collected in connection with a specific activity is stored for a period relative to such activity to be undertaken by an individual, as exemplified in the example given above. In the example given above, the DNA sample is stored for the anticipated period of travel of a traveler. In another embodiment, the DNA sample is stored for a fixed term that is not related to any activity to be carried out by the individual. For example, an insurance company may institute a program in which customers purchasing life insurance would have to provide a DNA sample to be stored during the coverage period (e.g., 1 year, or as long as the policy is renewed) as one of the prerequisites for insurance coverage. In the event positive identification of a deceased is required before payment of a life insurance policy, the DNA sample is retrieved and used to identify the deceased.

In a further embodiment, the insurance company may require the insured to notify the company of the timing of the activity covered under the insurance policy, prior to undertaking the activity, (e.g., travel by airline, dangerous activities, or other activities designated by the insurance company to require such notification by the insured). In the event the insured is killed in an accident as a result of any of such covered activities, the insurance company can quickly rely on the stored DNA sample for positive identification of the insured. The insurance company may collect the DNA samples by one of the methods described in the earlier embodiments.

Organizations other than insurance companies may also institute a program and process in which DNA samples are routinely collected from an individual associated with the organizations or transacting business with the organizations. For example, organizations such as schools, armed forces, businesses, etc. may wish to collect DNA samples from students, soldiers, customers and/or executives of the respective organizations.

In the foregoing embodiments, instead of and in addition to storing the DNA sample for future identification purposes, it may be processed shortly after sample collection (Block 200) to obtain personal DNA information (Block 210) (i.e., the DNA code). Such information is stored at a databank (Block 220), which may be maintained by the DNA processing facility or another entity. The DNA information may be made available to the customer or her agent as a means of personal identification, or for other personal use such as incorporating the DNA code in a souvenir or gift for friends and relatives (Block 230). The gift or souvenir has special meaning because they represent a part of the person from whom the DNA code was extracted.

In summary the present invention provides a method of collecting sample DNA that is non-invasive, allows rapid and positive personal identification of the accident victim, and does not disturb grieving family members by asking for reference samples for identification. The DNA sample is placed in a short-term or long-term storage and is promptly disposed of, once the individual completes his/her activity term. This requires less complex processes and attention than for other types of biological fluids.

It is appreciated that detailed discussion of the actual implementation of each step is not necessary for an enabling understanding of the invention. While the invention has been described with respect to the described embodiments in accordance therewith, it will be apparent to those skilled in the art that various modifications and improvements may be made without departing from the scope and spirit of the invention. Accordingly, it is understood that the invention is not to be limited by the specific illustrated embodiments, but only by the scope of the appended claims.

What is claimed is:

1. A process for collecting and storing a DNA sample of an individual, comprising the steps of:

collecting the DNA sample from the individual and depositing the DNA sample at an air travel departure terminal from where the individual departs on air travel activity that could potentially lead to accidental death; and storing the DNA sample that has been collected for future retrieval in the event of accidental death of the individual.

2. The process as in claim 1, wherein the DNA sample is collected from the individual using a non-invasive method.

3. The process as in claim 2, wherein the DNA sample is collected from the individual by means of a saliva sample.

4. The process as in claim 1, wherein the DNA sample is collected from the individual and deposited using an automated machine at the air travel departure terminal.

5. The process as in claim 1, wherein the DNA sample is collected from the individual and placed in a drop box at the air travel departure terminal.

6. The process as in claim 1, wherein the DNA sample is collected from the individual by an agent at the air travel departure terminal.

7. The process as in claim 1, wherein the DNA sample is discarded after a period relative to said activity.

8. A process for vending insurance to an individual, comprising the steps of:

offering insurance to the individual at an air travel departure terminal from where the individual departs on air travel activity that could potentially lead to accidental death; and collecting a DNA sample from the individual at said air travel departure terminal as a prerequisite for insurance coverage, whereby the DNA sample is stored for future retrieval in the event of accidental death of the individual.

9. The process as in claim 8, further comprising the step of depositing the DNA sample using an automated machine at the air travel departure terminal.

10. The process as in claim 8, wherein the step of collecting is implemented by an agent.

11. A method for vending insurance, comprising the step of:

providing automated machines at an air travel departure terminal from where individuals depart on air travel activities that could potentially lead to accidental death, said automated machines configured to vend insurance to the individuals and to deposit DNA samples collected from the individuals, whereby the DNA sample is stored for future retrieval in the event of accidental death of the individual depositing DNA samples from said individuals in said automated machines; and vending insurance to said individuals.

12. The method as in claim 11, wherein storing the DNA samples further comprises collecting said DNA samples from the automated machines and storing said DNA samples at a storage facility in a controlled environment.

13. A process for vending insurance to an individual, comprising the steps of:

offering insurance to the individual departing from an air travel departure terminal on an air travel activity that could potentially lead to accidental death; and collecting a DNA sample from the individual and depositing the DNA sample using an automated machine, whereby the DNA sample is stored for future retrieval in the event of accidental death of the individual.

14. A process for collecting and storing a DNA sample of an individual, comprising the steps of:

providing an automated machine at an air travel departure terminal, said automated machine configured to collect DNA samples from the individual;

collecting DNA samples from the individual using said automated machine; and storing the collected DNA sample.

\* \* \* \* \*